United States Patent [19]

Fuisz

[11] Patent Number: 5,427,804
[45] Date of Patent: Jun. 27, 1995

[54] LOW-FAT EDIBLE PROTEINS WITH MALTODEXTRINS AND LOW-SATURATE OILS

[75] Inventor: Richard C. Fuisz, Great Falls, Va.

[73] Assignee: Fuisz Technologies Ltd., Chantilly, Va.

[21] Appl. No.: 213,464

[22] Filed: Mar. 15, 1994

Related U.S. Application Data

[63] Continuation of Ser. No. 858,677, Mar. 27, 1992, abandoned, which is a continuation-in-part of Ser. No. 847,595, Mar. 5, 1992, Pat. No. 5,387,431, which is a continuation-in-part of Ser. No. 851,650, Mar. 16, 1992, Pat. No. 5,236,734.

[51] Int. Cl.⁶ ............................................... A23L 1/48
[52] U.S. Cl. ..................................... 426/99; 426/658; 426/646
[58] Field of Search .................. 426/580, 658, 598, 99, 426/98, 646, 656

[56] References Cited

U.S. PATENT DOCUMENTS

| | | |
|---|---|---|
| 2,826,169 | 3/1958 | LeVeen . |
| 2,918,404 | 12/1959 | Mende et al. . |
| 3,019,745 | 2/1962 | DuBois et al. . |
| 3,036,532 | 5/1962 | Bowe . |
| 3,067,743 | 12/1962 | Merton et al. . |
| 3,070,045 | 12/1962 | Bowe . |
| 3,073,262 | 1/1963 | Bowe . |
| 3,095,258 | 6/1963 | Scott . |
| 3,131,428 | 5/1964 | Mika . |
| 3,308,221 | 3/1967 | Opfell . |
| 3,324,061 | 6/1967 | Tanquary et al. . |
| 3,557,717 | 1/1971 | Chivers . |
| 3,595,675 | 7/1971 | Ash et al. . |
| 3,615,671 | 10/1971 | Schoaf . |
| 3,625,214 | 12/1971 | Higuchi . |
| 3,723,134 | 3/1973 | Chivers . |
| 3,762,846 | 10/1973 | Chivers . |
| 3,856,443 | 12/1974 | Salvi . |
| 3,875,300 | 4/1975 | Homm et al. . |
| 3,925,525 | 12/1975 | LaNieve . |
| 3,930,043 | 12/1975 | Warning et al. . |
| 3,951,821 | 4/1976 | Davidson . |
| 3,967,623 | 7/1976 | Butterworth et al. . |
| 3,992,265 | 11/1976 | Hansen . |
| 4,090,920 | 5/1978 | Studer, Jr. . |
| 4,104,406 | 8/1978 | Stringer ........................... 426/99 |
| 4,104,407 | 8/1978 | Stringer ........................... 426/99 |
| 4,136,145 | 1/1979 | Fuchs et al. . |
| 4,153,512 | 5/1979 | Messner et al. . |
| 4,293,570 | 10/1981 | Vadasz . |
| 4,303,684 | 12/1981 | Pitchon et al. . |
| 4,371,516 | 2/1983 | Gregory et al. . |
| 4,376,743 | 3/1983 | Dees . |
| 4,414,229 | 11/1983 | Bakal ................................ 426/98 |
| 4,492,685 | 1/1985 | Keith et al. . |
| 4,496,592 | 1/1985 | Kuwahara et al. . |
| 4,500,546 | 2/1985 | Turbak et al. . |
| 4,511,592 | 4/1985 | Percel ............................. 426/646 |
| 4,526,525 | 7/1985 | Oiso et al. . |
| 4,585,797 | 4/1986 | Cioca . |
| 4,615,892 | 10/1986 | Morehouse ........................ 426/98 |
| 4,619,833 | 10/1986 | Anderson . |

(List continued on next page.)

FOREIGN PATENT DOCUMENTS

| | | |
|---|---|---|
| 88/2770 | 4/1988 | South Africa . |
| 88/2771 | 4/1988 | South Africa . |
| 89/9318 | 12/1989 | South Africa . |
| 90/2139 | 3/1990 | South Africa . |
| 85-03414 | 8/1985 | WIPO ................................ 426/98 |

OTHER PUBLICATIONS

Low-Fat Lowdown Special Report, *Meat Processing*, 54–64 (Oct. 1991).

*Primary Examiner*—Carolyn Paden
*Attorney, Agent, or Firm*—Hoffmann & Baron

[57] ABSTRACT

Protein-based products such as hamburgers or soy-based materials are formed containing a combination of maltodextrin and an oleaginous substance. In a preferred embodiment, the protein-based products contain lower levels of saturated fat yet maintain the taste and mouthfeel of traditional products. Methods of preparing such products are also disclosed.

37 Claims, No Drawings

U.S. PATENT DOCUMENTS

| | | | |
|---|---|---|---|
| 4,640,837 | 2/1987 | Coleman | 426/93 |
| 4,689,235 | 8/1987 | Barnes | 426/89 |
| 4,738,865 | 4/1988 | Morres | 426/103 |
| 4,752,494 | 6/1988 | Tang | 426/94 |
| 4,793,782 | 12/1988 | Sullivan . | |
| 4,844,921 | 7/1989 | Bakal | 426/98 |
| 4,855,326 | 8/1989 | Fuisz . | |
| 4,873,085 | 10/1989 | Fuisz . | |
| 4,885,281 | 5/1989 | Hanstein et al. . | |
| 4,981,707 | 1/1991 | Morris | 426/93 |
| 4,997,856 | 3/1991 | Fuisz . | |
| 5,011,532 | 4/1991 | Fuisz . | |
| 5,028,632 | 7/1991 | Fuisz . | |
| 5,034,421 | 7/1991 | Fuisz . | |
| 5,096,492 | 3/1992 | Fuisz . | |
| 5,098,728 | 3/1992 | Singer | 426/580 |
| 5,158,798 | 10/1992 | Fung | 426/598 |
| 5,173,322 | 12/1992 | Melachouris | 426/580 |
| 5,236,734 | 8/1993 | Fuisz | 426/646 |
| 5,286,513 | 2/1994 | Fuisz | 426/641 |

LOW-FAT EDIBLE PROTEINS WITH MALTODEXTRINS AND LOW-SATURATE OILS

This application is a continuation of U.S. Ser. No. 07/858,677 filed Mar. 27, 1992, now abandoned, which is a continuation in part of U.S. Ser. No. 07/847,595 filed Mar. 5, 1992, now U.S. Pat. No. 5,387,431 and a continuation-in-part of U.S. Ser. No. 07/851,650 filed Mar. 16, 1992, now U.S. Pat. No. 5,236,734.

BACKGROUND OF THE INVENTION

The present invention relates to improvements in food products. In particular, the invention relates to protein-based products with enhanced flavor and reduced levels of fats and saturated oils.

Food technology in recent years has focused on providing high quality food products which are low in calorie content and low in cost. The public has become increasingly aware of the need to reduce fat intake from the diet. Lower fat foods, however, have tended to be rather bland and consumers, for the most part, have not been enthusiastic about such products due to their unappealing taste and texture.

One way to reduce the amount of fat in the diet is to avoid high fat meats. To this end, various efforts have been undertaken to reduce the fat content of meat products. Consumers have been increasing their consumption of leaner cuts of meat in order to reduce fat intake. Leaner cuts of meat, however, are costly and are not necessarily the most tasty. A certain amount of fat is thought to be needed during cooking to provide a tender and juicy product and customary mouthfeel.

Another suggestion to reduce the amount of fat in the diet has been to add materials such as carrageenan and/or soybean byproducts to meats. Consumers, however, have found such meat products to be lacking in taste, rather dry and generally undesirable. Thus, the public awaits more desirable alternatives.

Carbohydrates have always been a major component of the human diet. Sugars, in particular, have been used extensively as a food ingredient. Materials containing both simple sugars and polymers of saccharides have also been used as ingredients in food products. Food grade saccharides are available as mono-, di-, tri-, tetra-, pentasaccharides, oligomers, and as carbohydrates having a large number of monosaccharide molecules, e.g., greater than 10 monosaccharide units, which are known as polysaccharides.

Saccharide-based products can have varying degrees of low-monomer saccharides, or sugars, oligomers, and polysaccharides such as starch. Some saccharide-based products are prepared by hydrolysis of starch and are classified by the degree of starch polymer hydrolysis. The measuring unit is referred to as D.E. or dextrose equivalent. D.E. is defined as reducing sugars expressed as dextrose, and is reported as a percentage of the dry substance.

A saccharide-based product having high short-carbon-chain content, e.g., glucose and low-unit oligomers thereof, usually results in a higher dextrose equivalent, (D.E.). However, saccharide-based material having greater long-carbon-chain content, e.g., high monomer unit oligomers and polymers usually results in a lower D.E. rating.

Maltodextrins, for example, contain a mix of sugars and polysaccharides which range from long-chain oligomers resulting from starch hydrolysis to sugars having a low number of monomeric units. Under FDA guidelines, maltodextrin consists of non-sweet, nutritive saccharide polymers having a D.E. of less than 20. Corn syrup solids, regarded by the FDA as having a D.E. of greater than 20, is a similar polysaccharide-based product. The present inventor, however, refers to maltodextrins as including both such saccharide-based materials.

Maltodextrins have been used as a nonfat additive. One of the greatest advantages of maltodextrins is that they do not act adversely on the intestinal tract. Consequently, they are particularly useful as a bulking agent and as a fat substitute. Moreover, maltodextrins are generally recognized as safe (GRAS) by the United States Food and Drug Administration.

Thus, in view of the shortcomings associated with currently available low-fat food products, artisans still seek to make low-fat alternatives such as meat products and edible protein compositions more desirable to the consuming public. It is, therefore, an object of the present invention to provide reduced-fat food products which have the taste, texture and gustatory qualities of higher fat-containing products without the fat or its deleterious effects.

Other and further objects of the present invention will become apparent from the following description and its scope will be pointed out in the appended claims.

SUMMARY OF THE INVENTION

The present invention is a protein-based food product which includes a combination of maltodextrin and an oleaginous substance. The combination can be provided by mixing the two ingredients prior to introducing it to a proteinaceous material which forms the bulk of the product. Another embodiment contemplates that the combination be formed by spraying an oleaginous substance on the maltodextrin prior to combining it with the proteinaceous material.

The present invention is also directed to the combination of maltodextrin and oleaginous material itself, which is used as an additive to enhance the protein-based food product. The oleaginous substance used in the product can be selected from the group consisting of vegetable oils, soy bean oil, canola oil, corn oil, sunflower oil, olive oil, peanut oil, palm oil, cottonseed oil, safflower oil, coconut oil, and mixtures thereof. Alternatively, the oleaginous material can be selected from animal fats, tallows, lards, fish oils, crustacean oils, and mixtures thereof.

In a preferred embodiment of the present invention, the maltodextrin, usually in granulated form, can be mixed with the oleaginous substance in the presence of an aqueous medium, e.g., water, in an amount sufficient to form a dispersion before incorporating it in the food product. Advantageously, it has been found that the dispersion formed is of high quality and that the oleaginous substance resists separation from the aqueous medium. This enhances both the ability to achieve thorough mixing with the proteinaceous material, and to retain a consistent mixture throughout the end product.

The combination of maltodextrin and oleaginous substance can have a composition of from about 70% to about 99.5% by weight of maltodextrin and from about 0.5% to about 30% by weight of the oleaginous substance. Preferably, the maltodextrin is present in an amount of from about 75% to about 90%, whereas the oleaginous substance is present in an amount of from about 10 to 25% of the combination.

When included in a food product, the combination can be present in an amount of from about 0.5% to about 25% by weight of the food product, and is preferably present in an amount of from about 5% to about 10% of the end product.

The proteinaceous material used in the product can be selected from the group consisting of animal meats, soy-based products, vegetable-based products, fish products, crustacean products, and mixtures thereof.

In yet another preferred embodiment of the present invention, a flavorant selected from natural and artificial flavors and mixtures thereof can also be included in the additive as well as the end product. In a preferred manifestation of this embodiment, the flavorant is incorporated in the oleaginous material.

In one most preferred embodiment of the present invention, the oleaginous material is less than 30% saturated, preferably less than 20% saturated, and most preferably, less than 15% saturated.

It should further be noted that the present invention can include a frozen protein product such as a frozen meat patty. This product is made by combining the proteinaceous material, such as ground beef, at a temperature above freezing but below 5° C. after which the mixture is frozen. The mixed composition is preferably flash frozen to a temperature lower than −5° C. A preferred method of making the frozen product includes the use of shaved or crushed ice added to the mixture prior to freezing.

As a result of the present invention, protein-based food products such as meat patties can be provided with a reduced saturated fat content while retaining an acceptable organoleptic appearance, texture and taste.

The present invention is especially useful in providing an expedient for reducing the saturated fats without the necessity of an additional manufacturing process, e.g., flash flow of the maltodextrin as in application Ser. No. 07/847,595 filed Mar. 5, 1992, now U.S. Pat. No. 5,387,431.

For a better understanding of the present invention together with other and further objects, reference is made to the following description. The scope of the invention will be set forth in the appended claims.

DETAILED DESCRIPTION OF THE INVENTION

The present invention concerns formation of enhanced protein-based food products and additives designed for providing lower fat content protein-based food products. The additive contains maltodextrins and oleaginous substances. Maltodextrins are composed of water-soluble glucose-based polymers obtained from the reaction of starch with enzymes or acid in the presence of water. The hydrolysis reaction produces a carbohydrate mixture of saccharides having a dextrose equivalence (D.E.) of less than 40. In one embodiment of the invention, the D.E. is between 20 and 40. These maltodextrin products have been classified by the FDA as corn syrup solids. In another embodiment, the D.E. is between 10 and 20. The maltodextrins useful in the present invention include some products sold under the trademark MALTRIN ® by the Grain Processing Corporation of Muscatine, Iowa or "Dri-Sweet" variety of maltodextrins sold by the Hubinger Company of Keokuk, Iowa. Such products are available as powders, granules or the like.

The additive also includes an oleaginous substance. A non-limiting list of such substances include vegetable oils, soybean oil, canola oil, corn oil, sunflower oil, olive oil, peanut oil, palm oil, cottonseed oil, safflower oil, coconut oil and the like, and mixtures thereof. In a preferred aspect, the oleaginous substance and, consequently, food products prepared therewith, are preferably high in polyunsaturated fats and contain reduced or lack saturated fats. In this regard, the oleaginous materials preferably contain less than 30% saturated fats, with amounts of less than 20% being preferred and amounts of less than 15% being most preferred. The food additive, thus, advantageously allows the artisan to substitute or exchange "healthier" oils for a portion of the unhealthy saturated fats typically present in protein-based products without noticeably detracting from the organoleptic qualities.

In one aspect of the invention, the maltodextrin and oleaginous substance are mixed prior to being added to the proteinaceous material to form the protein-based food product. The oleaginous material and maltodextrin can be combined by physical mixing of the two ingredients. The ingredients can be combined using a blender or any technique known in the art. The maltodextrin and oleaginous substance can be mixed as a dispersion. The dispersion is formed by contacting the combination of ingredients with an aqueous medium. The dispersion allows the combination to be mixed with proteinaceous materials so that a substantially homogeneous mixture of all ingredients is obtained. The dispersion may also be injected or otherwise introduced into ground or unground meats or protein-based materials to enhance its organoleptic qualities.

In another embodiment, the combination is prepared by spraying the oleaginous substance on the maltodextrin. Spraying can be carried out using techniques known in the art such as fluidized bed techniques. The combination is then mixed with the meat or other protein-based material to form the food product.

The combination of maltodextrin and oleaginous substance in the food additive can contain maltodextrin, in amounts of from about 70% to about 99.5% by weight, with amounts of from about 75% to about 90% being preferred. The oleaginous substance, on the other hand, makes up from about 0.5% to about 30% by weight of the combination, with amounts of from about 10% to about 25% of the combination being preferred.

The protein-based food products and novel additive designed for enhancing protein-based food products can also be prepared with additional components. Such additional components are primarily food related and do not detract from the appearance or taste of food products or the enhancing additive. The nature and amount of the additional materials will vary and are generally within the skill of the artisan.

Thus, in one aspect of the invention, ingestible food and/or food ingredient materials can be included with the food products. For example, a broad range of natural and artificial flavor compositions and mixtures thereof are suitable. The flavors can be spices such as onion, garlic, salt, pepper and so forth. Also contemplated are natural and/or artificial flavors. Ideally, the oleaginous substance can be flavored by incorporation of the flavorant directly in the oleaginous material prior to further mixing. However, it is contemplated that any flavorant suitable for inclusion with protein-based food products can be used herein. Those skilled in the art will realize that the number and amount of flavorant(s) will depend upon the flavorant(s) selected and the preference of the artisan.

The food products prepared in accordance with the present invention can also include a broad range of adjunct or ancillary materials. For example, food sauce materials, condiments, gravy mixes, nutritional supplements, low-calorie food materials, food conditioning agents, dehydrated vegetable and/or animal fluids, vitamins and/or minerals, preservatives, emulsifiers, colorants, dyes and the like, and mixtures thereof can be included. Such materials may be included in addition to or in lieu of any additional component materials described above. Any such material can be either combined with the maltodextrin and oleaginous material or admixed with the protein material separately.

Those skilled in the art will realize that the above lists are merely illustrative and not intended to exclude ingredients known to be within the scope of edible ingredients. Further, the amount and combination of edible ingredients will depend upon the particular ingredients selected and the preference of the artisan.

In a further aspect of the invention, the combinations of maltodextrin and oleaginous substance are prepared by including a fat or fatty-based ingredient. For example, an edible animal fat such as beef, pork, lamb, poultry-based fats or similar animal fats or mixtures thereof can be used. Similarly, fat-containing materials such as beef tallow, sheep tallow, butter or lards, hydrogenated animal and/or vegetable oils may be included. Further, fish or crustacean-based oils or oleaginous materials are also useful. Combinations of the above-described materials are also contemplated. The invention also contemplated blends of these materials with the relatively unsaturated oils discussed above.

The maltodextrin/oleaginous substance combination is especially well-suited for protein-based food products, and preferably, products containing at least 60% edible protein. The combination additive is present in the products in amounts of from about 0.5% to about 25% by weight, with amounts of from about 5% to about 10% being preferred. While the maltodextrin and oleaginous substance are preferably combined prior to admixing with proteinaceous material, the novel combination of maltodextrin and oleaginous material can be formed in situ.

The proteinaceous material which forms the bulk of the inventive food products and combined with the enhancing maltodextrin/oleaginous mixture includes meat products: animal meats such as beef, pork, lamb, mutton, and horse; poultry products, such as turkey, chicken or capon, and so forth. Fish, crustacean-based and/or protein-based compositions such as soy or vegetable products and mixtures of the above are also contemplated. Thus, the artisan is able to provide a wide array of enhanced products. In one aspect, inexpensive fish meat such as pollack can be enhanced to provide taste characteristics associated with more expensive grades of fish, i.e., crab legs. In addition, the additive can be prepared to contain butter, butter flavors and spices which, therefore, can be efficiently incorporated into fish products to provide enhanced seafoods and seafood-like products.

In an alternative aspect of the invention, it is also contemplated that the novel additive can be included in most processed meat products, especially those which normally include a substantial level of fat in order to obtain a desired taste characteristic. For example, hot dogs, sausages, bratwursts, beef jerky, pet foods and the like may be prepared to include the novel additive and thus substantially lower the fat content. It has been surprisingly found that exceptionally tasty meat or protein-based meat-like products can be prepared by exchanging a portion of the fat typically found in such products with the novel food additive. In this aspect, the accustomed flavor and lubriciousness is achieved with a significantly reduced fat content. Such attributes are particularly observable when lightly hydrogenated oils are included. Thus, protein-based food products can be prepared to provide most of the same organoleptic qualities but with substantially less fat in the overall product.

An additional advantage of the present invention is the ability of maltodextrin to extend the shelf-life of food products. While applicant is not bound by theory, it appears that maltodextrins have an antioxidant and bactericidal effect on edible proteins when incorporated therein. The extended shelf-life is observed in ground meats such as ground chicken, ground turkey, and ground beef and is especially advantageous property when the bulk protein material has low salt levels.

In yet a further aspect of the invention, the maltodextrin/oleaginous combination and proteinaceous material are mixed at a temperature above freezing but below 5° C. The ingredients are mixed at this temperature range before being promptly frozen. In particular, the maltodextrin/oleaginous combination is added to ground proteinaceous material such as ground meat held at substantially the freezing point, e.g. below 5° C., and then the mixture is promptly frozen and preferably flash frozen to a temperature lower than −5° C. If water is included the protein-based food product, it may be added as shaved or crushed ice prior to the freezing step. When the frozen patties prepared in this manner are flame broiled, fried or microwaved, the patties have more retained liquids as compared to pressed solids and have improved taste, texture and mouthfeel.

EXAMPLES

The following examples serve to provide further appreciation of the invention but are not meant in any way to restrict the effective scope of the invention.

Example 1

Twenty (20) grams of canola oil was added gradually to eighty (80) grams of maltodextrin (Hubinger Dri-Sweet-36) and mixed thoroughly. The mixture was added to water and stirred slowly. The water was cloudy, showing evidence of a fine dispersion of the oil. The dispersion remained stable with very little accumulation of oil on the surface until over an hour later.

As a comparison, twenty (20) grams of canola oil was added to the same amount of water and agitated vigorously for several minutes. The mixture first appeared cloudy, but within seconds, phase separation appeared. After a few minutes, most of the canola oil accumulated on top of the water.

Example 2

| OIL/MALTODEXTRIN MIXTURE IN GROUND BEEF | |
|---|---|
| Ingredients | Weight (%) |
| Maltodextrin (Hubinger Dri-Sweet-36) | 80 |
| Canola Oil | 20 |

In this example, a mixture was prepared by slowly adding the canola oil to the maltodextrin while stirring until a thorough mixture was obtained. The mixture was mixed with ground beef as set forth in Table I.

TABLE I

| Hamburger Sample | | Prefried Weight (Grams) | Pressed Weight of Fried Sample (Grams) | Weight of Liquids from Fried Sample (Grams) | Ratio of Liquids to Solids |
|---|---|---|---|---|---|
| A) | Hamburger with 27% Beef Fat | 144 | 73.5 | 42.3 | 0.576 |
|  | Water | 6 | | | |
| B) | Hamburger with 10% Beef Fat | 144 | 84.9 | 38.1 | 0.449 |
|  | Water | 6 | | | |
| C) | Hamburger with 10% Beef Fat | 138 | 78.2 | 42.9 | 0.549 |
|  | Water | 6 | | | |
|  | Oil/ Maltodextrin Mixture | 6 | | | |

The beef hamburger compositions set forth in the table were pressed in a 4-inch square hamburger press to form patties. The patties were fried on an electric skillet set at 350° F. for three minutes on each side and thereafter analyzed. The samples were pressed in a two-stage potato press to extract liquids to determine liquid or juiciness content.

The sample containing the oil/maltodextrin mixture and corresponding reduced amount of hamburger was more juicy, i.e., had a higher pressed liquid to solid ratio than the patty which contained 10% beef fat. The ratio of liquids to solids in the inventive sample was nearly identical to that provided by the hamburger made with 27% fat. Moreover, the appearance, texture and mouthfeel of the low-fat hamburger was judged to be better than that of the low-fat hamburger and virtually identical to the high-fat hamburger.

Example 3

| OIL/MALTODEXTRIN MIXTURE IN GROUND TURKEY | |
|---|---|
| Ingredients | Weight (%) |
| Maltodextrin (Hubinger-Dri-Sweet-36) | 80 |
| Canola Oil | 20 |

In this example the oil/maltodextrin mixture was prepared as in Example 2. Turkeyburger compositions were prepared as set forth in Table II and pressed in a 4-inch square hamburger press to form patties. The patties were fried in an electric skillet at 350° F. for a total of six minutes on each side, flipping every three minutes and analyzed. The samples were pressed in a two-stage potato press to extract liquids to determine liquid or juiciness content.

TABLE II

| Sample | Prefried Weight (Grams) | Pressed Weight of Fried Sample (Grams) | Weight of Liquids from Fried Sample (Grams) | Ratio of Liquids to Solids |
|---|---|---|---|---|
| A) Turkeyburger with 7% Fat | 150 | 97.8 | 17.0 | 0.17 |
| B) Turkeyburger with 7% Fat | 144 | 93.3 | 25.7 | 0.295 |
| Oil/ Maltodextrin Mixture | 6 | | | |

The samples containing the oil/maltodextrin mixture and corresponding reduced amount of turkeyburger had substantially higher weights of juice when compared to the control. Further, the ratio of liquids to solids in the inventive samples was almost twice as much as the reduced-fat turkeyburger. The flavor, texture, and mouthfeel of the inventive sample were judged to be preferred by a wide margin.

Example 4

In this example, the procedure of Example 3 was repeated using beef-flavored canola oil obtained from Bunge Foods in place of the unflavored canola oil in the mixture. The turkeyburgers prepared with this combination exhibited enhanced juiciness over the controls and delivered a pleasant beef flavor.

The present invention provides the food manufacturer with a simple expedient for fat reduction in protein-based products without sacrificing organoleptic quality or incurring significant additional expense.

While there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

What is claimed is:

1. A food product comprising an admixture of maltodextrin and an oleaginous substance mixed with a third ground component selected from the group consisting of animal meats, soy-based products, vegetable based products, fish products, crustacean products, poultry products and mixtures thereof, wherein said maltodextrin is present in an amount from about 70% to about 99.5% by weight of said admixture, and said oleaginous substance is present in an amount of from about 0.5% to about 30% by weight of said admixture.

2. The food product of claim 1, wherein said third component is at least 60% of said food product.

3. The food product of claim 1 wherein said combination of maltodextrin and said oleaginous substance is provided by mixing before introducing to said protein-based food product.

4. The food product of claim 1 wherein said oleaginous substance is sprayed onto said maltodextrin.

5. The food product of claim 1, wherein said oleaginous substance is less than 30% saturated.

6. The food product of claim 5, wherein said oleaginous substance is less than 20% saturated.

7. The food product of claim 6, wherein said oleaginous substance is less than 15% saturated.

8. The food product of claim 1, wherein said oleaginous substance is selected from the group consisting of vegetable oils, soybean oil, canola oil, corn oil, sunflower oil, olive oil, peanut oil, palm oil, cottonseed oil, safflower oil, coconut oil, and mixtures thereof.

9. The food product of claim 1, wherein said oleaginous material is selected from the group consisting of animal fats, tallows, lards, fish oils, crustacean oils, and mixtures thereof.

10. The food product of claim 1, wherein said oleaginous material is selected from the group consisting of vegetables oils, soybean oil, canola oil, corn oil, sunflower oil, olive oil, peanut oil, palm oil, cottonseed oil, safflower oil, coconut oil, animal fats, tallow, lards, fish oils, crustacean oils, and mixtures thereof.

11. The food product of claim 1, wherein said maltodextrin and said oleaginous substance are contacted in the presence of an aqueous medium sufficient to form a dispersion before including in said food product.

12. The food product of claim 1, wherein said maltodextrin is present in an amount of from about 75% to about 90% and said oleaginous is present in an amount of from about 10% to about 25% of said combination.

13. The food product of claim 1, wherein the combination of said maltodextrin and said oleaginous substance is present in an amount of from about 0.5% to about 25% by weight of said food product.

14. The food product of claim 13, wherein said combination is present in an amount of from about 5% to about 10% by weight.

15. The food product of claim 1, wherein the source of protein for said product is selected from the group consisting of animal meats, soy-based products, vegetable-based products, fish products, crustacean products and mixtures thereof.

16. The food product of claim 1, further comprising a flavorant selected from the group consisting of natural flavors, artificial flavors and mixtures thereof.

17. The food product of claim 16, wherein said flavorant is included in said oleaginous material.

18. A method of preparing a protein-based food product, comprising adding a combination of an oleaginous substance and maltodextrin with a proteinaceous material to provide said protein-based product, wherein said combination is prepared by spraying said oleaginous material on said maltodextrin before adding to said proteinaceous material.

19. The method of claim 18, wherein said maltodextrin and said oleaginous substance are contacted in the presence of an aqueous medium to form a dispersion.

20. The method of claim 19, wherein said proteinaceous material is contacted with said combination in situ.

21. The method of claim 18, wherein said oleaginous substance is selected from the group consisting of vegetable oils, soybean oil, canola oil, corn oil, sunflower oil, olive oil, and mixtures thereof.

22. The method of claim 18, wherein said oleaginous material is selected from the group consisting of animal fats, tallows, lards, fish oils, crustacean oils, and mixtures thereof.

23. The method of claim 18, wherein said oleaginous material is selected from the group consisting of vegetable oils, soybean oil, canola oil, corn oil, sunflower oil, animal fats, tallows, lards, fish oils, crustacean oils, and mixtures thereof.

24. The method of claim 18, wherein said oleaginous substance is present in an amount of from about 0.5% to about 30% by weight of said combination, and said maltodextrin is present in an amount of from about 70% to about 99.5% by weight.

25. The method of claim 24, wherein said oleaginous substance is present in an amount of from about 10% to about 25% by weight and said maltodextrin is present in an amount of from about 75% to about 90% by weight.

26. The method of claim 18, wherein said proteinaceous material is selected from the group consisting of animal meats, soy-based products, vegetable-based products, fish products, crustacean products and mixtures thereof.

27. The method of claim 18, wherein said combination is added in an amount of from about 0.5% to about 25% by weight of said product.

28. The method of claim 27, wherein said combination is added in an amount of from about 5% to about 10% of said product.

29. The method of claim 18, further comprising a flavorant selected from the group consisting of natural flavors, artificial flavors and mixtures thereof.

30. The method of claim 29, wherein said flavorant is included in said oleaginous substance.

31. The product made by claim 18.

32. A method of preparing a protein-based food product, comprising adding a combination of an oleaginous substance and maltodextrin with a proteinaceous material to provide said protein-based product; and mixing said combination and said proteinaceous material maintained at a temperature of above freezing but below 5° C. and then promptly freezing the mixed composition, wherein said proteinaceous material is ground meat.

33. The product made by claim 32.

34. A method of preparing a protein-based food product, comprising adding a combination of an oleaginous substance and maltodextrin with a proteinaceous material to provide said protein-based product; and mixing said combination and said proteinaceous material maintained at a temperature of above freezing but below 5° C. and then promptly freezing the mixed composition, which further comprises adding shaved or crushed ice to the mixture prior to said freezing.

35. A method of preparing a food product comprising mixing an admixture of an oleaginous substance and maltodextrin to a third ground component selected from the group consisting of animal meats, soy-based products, vegetable based products, poultry products, fish products, crustacean products and mixtures thereof at temperatures of above freezing but below 5° C. and promptly freezing the mixed composition.

36. The method of claim 35, wherein said third component is at least 60% of said food product.

37. The method of claim 35 wherein the mixed composition is flash frozen to a temperature lower than −5° C.

* * * * *